(12) United States Patent
Verwulgen et al.

(10) Patent No.: US 11,717,164 B2
(45) Date of Patent: Aug. 8, 2023

(54) TISSUE ELASTICITY MEASUREMENT (71) Applicant: UNIVERSITEIT ANTWERPEN, Antwerp (BE)

(72) Inventors: Stijn Verwulgen, Schoten (BE); Steven Truijen, Zoersel (BE); Jochen Vleugels, Antwerp (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 330 days.

(21) Appl. No.: 16/955,035

(22) PCT Filed: Dec. 18, 2018

(86) PCT No.: PCT/EP2018/085358
§ 371 (c)(1),
(2) Date: Jun. 17, 2020

(87) PCT Pub. No.: WO2019/121592
PCT Pub. Date: Jun. 27, 2019

(65) Prior Publication Data
US 2020/0375464 A1 Dec. 3, 2020

(30) Foreign Application Priority Data
Dec. 18, 2017 (EP) .................................. 17207883

(51) Int. Cl.
*A61B 5/00* (2006.01)
*A61B 5/30* (2021.01)
(52) U.S. Cl.
CPC .............. *A61B 5/0053* (2013.01); *A61B 5/30* (2021.01); *A61B 5/4312* (2013.01);
(Continued)

(58) Field of Classification Search
CPC ....... A61B 5/0053; A61B 5/30; A61B 5/4312; A61B 5/4878; A61B 5/6885;
(Continued)

(56) References Cited

U.S. PATENT DOCUMENTS

| | | | |
|---|---|---|---|
| 2004/0116834 A1 | 6/2004 | Steinberg | |
| 2015/0290454 A1 * | 10/2015 | Tyler | G06F 3/012 607/134 |

(Continued)

FOREIGN PATENT DOCUMENTS

| | | | | |
|---|---|---|---|---|
| CA | 2833518 A1 * | 5/2014 | .......... | A61B 5/0053 |
| DE | 2638893 A1 | 3/1977 | | |

(Continued)

OTHER PUBLICATIONS

Leonard et al., "Assessing the Spastic Condition of Individuals with Upper Motoneuron Involvement: Validity of the Myotonometer," Archives of Physical Medicine and Rehabilitation, vol. 82, Oct. 31, 2001, pp. 1416-1420.

(Continued)

*Primary Examiner* — Matthew Kremer
*Assistant Examiner* — Om Patel
(74) *Attorney, Agent, or Firm* — Workman Nydegger (57) ABSTRACT

A device for measuring elasticity of a tissue of an object is disclosed. It comprises a base portion comprising contact means for contacting the tissue. It also comprises a palpation probe for pushing down on the tissue comprising a palpation pen for pushing down the tissue and a force measuring means for determining a palpation force applied to the palpation probe and/or a displacement measuring means for determining a displacement of the palpation pen being representative for a displacement of the tissue. The device also comprises a swiveling handle mounted pivotally to the base portion for positioning the device and for distributing (Continued)

a positioning force along the at least two contact points in a predetermined manner.

15 Claims, 7 Drawing Sheets

(52) U.S. Cl.
CPC .......... *A61B 5/4878* (2013.01); *A61B 5/6885* (2013.01); *A61B 5/742* (2013.01); *A61B 5/7405* (2013.01); *A61B 5/7455* (2013.01); *A61B 2560/0223* (2013.01)

(58) Field of Classification Search
CPC ..... A61B 5/7405; A61B 5/742; A61B 5/7455; A61B 2560/0223; A61B 5/442; A61B 5/4519
See application file for complete search history.

(56) References Cited

U.S. PATENT DOCUMENTS

2016/0183800 A1* 6/2016 Schäffer ............... A61B 5/0053 606/130
2016/0310006 A1* 10/2016 Aguero Villarreal ........................ A61B 5/4538

FOREIGN PATENT DOCUMENTS

| DE | 4343612 A1 | 6/1995 | |
|---|---|---|---|
| WO | WO-2011049854 A1 * | 4/2011 | ............. A61B 5/053 |
| WO | WO-2012005701 A2 * | 1/2012 | ........... A61B 5/1107 |
| WO | WO-2014165049 A1 * | 10/2014 | ........... A61B 5/0062 |

OTHER PUBLICATIONS

Shiffman et al., "Electrical Impedance of Muscle during Isometric Contraction," Institute of Physics and Engineering in Medicine: Physiological Measurement, vol. 24, Feb. 3, 2003, pp. 213-234.

Kuwahara et al., "Quantification of Hardness, Elasticity and Viscosity of the Skin of Patients with Systemic Sclerosis Using a Novel Sensing Device (Vesmeter): A Proposal for a New Outcome Measurement Procedure," Rheumatology, vol. 47, Apr. 25, 2008, pp. 1018-1024.

Rutkove, "Electrical Impedance Myography: Background, Current State, and Future Directions," Muscle & Nerve, vol. 40, Dec. 31, 2009, pp. 936-946.

Ditroilo et al.,"The Effectiveness of Two Novel Techniques in Establishing the Mechanical and Contractile Responses of Biceps Femoris," Institute of Physics and Engineering in Medicine: Physiological Measurement, vol. 32, Jul. 15, 2011, pp. 1315-1326.

Pruyn et al., "Validity and Reliability of Three Methods of Stiffness Assessment," Journal of Sport and Health Science, vol. 5, Dec. 8, 2015, pp. 476-483.

"TMG Functional Muscle Strain Diagnostics," retrieved from http://www.tmg-bodyevolution.com/medical/functional-muscle-strain-diagnostics/, Sep. 30, 2017, 4 Pages.

Extended European Search Report from corresponding EP Application No. 17207883.4, dated May 24, 2018.

International Search Report and Written Opinion from PCT Application No. PCT/EP2018/085358, dated Apr. 26, 2019.

* cited by examiner

Frequency [Hz]
$F = f_{max}$
from signal spectrum

Decrement
$D = \ln(a_1/a_3)$

Stiffness [N/m]
$S = a_{max} \cdot m_{probe} / \Delta l$
$a_{max}$ = max acceleration
$m_{probe}$ = probe mass Stress relaxation time
[ms] $R = t_R - t_1$ Creepability
(Deborah number)
$C = R/(t_1 - t_T)$ Prior Art
FIG. 3

TISSUE ELASTICITY MEASUREMENT

TECHNICAL FIELD OF THE INVENTION

The present invention relates to the field of sports & health sciences and physiotherapy. More particularly, the present invention relates to systems and methods for measuring muscle stiffness and changes therein.

BACKGROUND OF THE INVENTION

Assessment of muscle condition is highly important in clinical, sub-clinical and daily life practice. For example, a real time assessment of muscle hardness is directly related to physical exercise and could be a valuable indicator thereof. It is also related to biomechanical performance, fatigue and recovery after sport performance. In particular elasticity of tissue is an important indicator in physiotherapy. Muscle stiffness, and changes thereof, does not only reflect physical activity, fitness or well-being, but it is also an indicator for muscular deficit. For example, enhanced muscle tone can cause pain and disability. Muscle hardness/tone also relates to neuro-muscular diseases such as ALS or Parkinson. Further, muscular activity in relation to motion capture (mocap) is highly relevant in research, e.g. biomechanical modelling.

Electromyography (EMG) is a common technique for monitoring muscular activity. With EMG, bio-signals such as fluctuations in electric potential are detected and acquired. To that end, electrodes should be placed near muscles. EMG is limited in time since it can only detect changes in muscular activity and also limited in outcome since it provides no quantitative data on muscular activity, merely discriminating "change in activity-no change in activity"

A typical and initiating, though not limitative, example in physiotherapy is the diagnosis, treatment and follow-up of a stiff neck (contracted trapezius). Current methods rely on the experience of the physiotherapist (palpation), range of motion and/or pain perception of patients (as explained in relation to the Modified Ashworth scale in Leonard C T, Stephens J U, Stroppel S L. "Assessing the spastic condition of individuals with upper motoneuron involvement: validity of the myotonometer". Archives of physical medicine and rehabilitation. 2001; 82(10):1416-20)

Daily practice reveals that they are highly unrepeatable and subject to various inter and intra subject other context parameters, such as physical fitness, age, body mass index, joint condition, etc., in case of assessments based on range of motion.

Another promising technique assesses muscular condition with electro impedance myography (EIM). EIM includes applying a high frequency alternating current through two electrodes placed onto the subject's skin; the current would circulate through the muscle. Document "Rutkove S B. Electrical impedance myography: background, current state, and future directions. Muscle & nerve. 2009; 40(6):936-46" and document "Shiffman C A, Aaron R, Rutkove S B. Electrical impedance of muscle during isometric contraction. Physiological measurement. 2003; 24(1):213" describes that the change in electric current resistance (by phase shift due to the contributions of the real current and complex current) gives an indication on muscular condition and deterioration, and even a measure for contraction under different loads.

Figure 1:
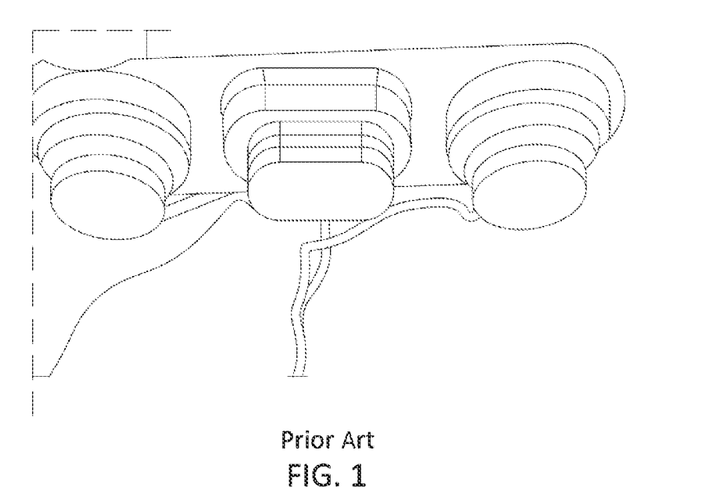
FIG. 1 illustrates a prototype concept for measuring muscle tone with EIM, as known from prior art.

FIG. 1 shows a used-friendly system developed by the inventors, in order to take those impedance measures. However, the published measurements could not be reproduced. Time sequence indicated that resistance has a heavy dependence of other uncontrolled parameters, and that current merely found its way onto the subject surface skin, rather than maintaining its presumed route through the muscle. It seems that hurdles exist in applying the theory based on the principle of EIM towards quantifying muscle activity, and assessment of muscle tone, for practical applications.

Thus, a different mechanical approach has been followed. This approach approximates the behaviour of a tissue, or muscle, to that of a string.

Figure 2:
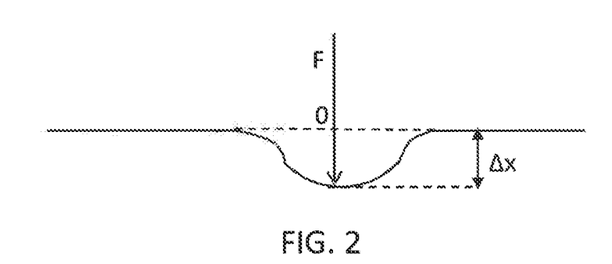
FIG. 2 illustrates the force and displacement of a string-like shaped body, as known from prior art.

Stiffness/hardness is primary related to the amount of displacement Delta x, when a probe (with a given area) is mechanically pressed with a predetermined force F, exerted substantially perpendicular on the concerned tissue, as shown in FIG. 2.

Under that condition, in a string (which can be considered a body with a single degree of freedom), the force factor k=F/Delta x is approximately constant. It can be taken as a measure for stiffness (N/m). This leads to a second order differential equation describing motion of the involved tissue of basic type (however, dampening mechanisms should be taken into account):

$$x''=kx$$

The solution is a periodic oscillation, e.g. sin ((sqrt k)*t), for the above basic type, so the force constant representing muscle stiffness can be measured by assessing frequency when a muscle is subject to an external force, causing a (periodic) vibration.

Figure 3:
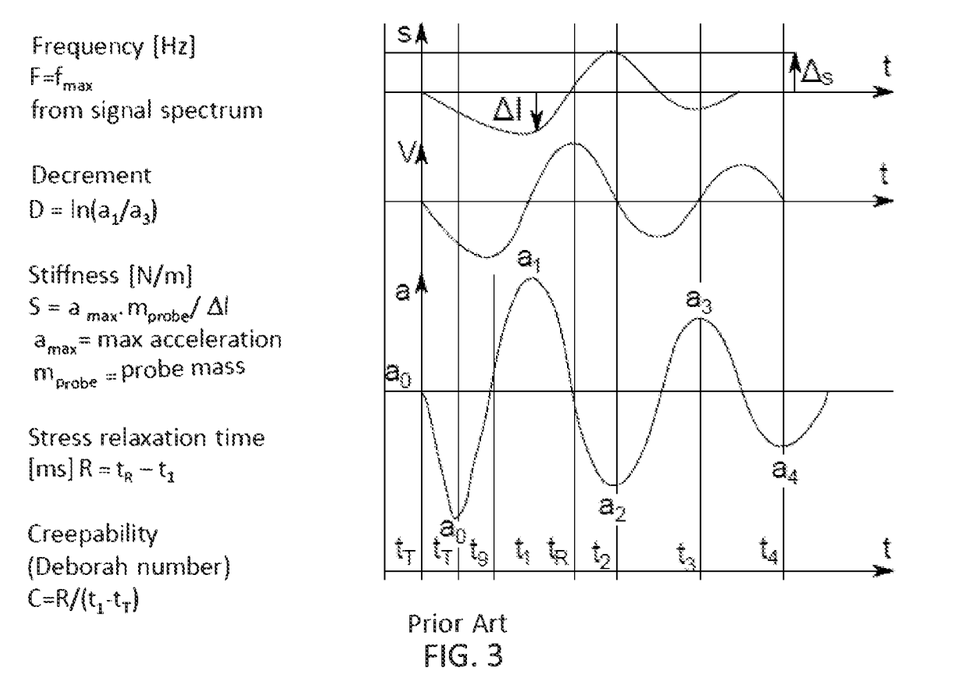
FIG. 3 illustrates a commercial measuring device and its typical readout, as known from prior art.

Already dedicated devices exist, which assess such kinematic properties of the muscle as indicators for mechanical muscle properties. For example, the prior art device "Myotonpro" shown in FIG. 3, upper photo, has a probe that applies a mechanical impact (during 15 ms, with a force of 0.3-0.4 N) after which the resulting damped oscillations are recorded via an in-built accelerometer, sampled at 3.2 KHz with an accuracy of 5% s (as described in Pruyn E C, Watsford M L, Murphy A J. "Validity and reliability of three methods of stiffness assessment." Journal of Sport and Health Science. 2015). Mechanical impact causes the muscle to deform locally for a few millimetres for a certain period of time. The response to the perturbation, in relation to applied force, is measured as an indicator for stiffness (as explained in Ditroilo M, Hunter A M, Haslam S, De Vito G. "The effectiveness of two novel techniques in establishing the mechanical and contractile responses of biceps femoris. Physiological measurement." 2011; 32(8):1315). Other wave characteristics can give information on muscle condition (FIG. 3, lower diagram).

"Myotonpro" retrieves kinematic data for stiffness, which is static in nature. Although it provides a local measurement, the damping might induce error, affecting accuracy and repeatability. Another major disadvantage is that the measurement principle does not reflect the way in which physiotherapists actually assess muscle tone or stiffness, which is by palpation rather than assessing kinematics. However, since frequency is a parameter independent of displacement induced by an operator, measurements of the frequency usually give high accuracy (as shown in Pruyn E C, Watsford M L, Murphy A J. "Validity and reliability of three methods of stiffness assessment". Journal of Sport and Health Science. 2015).

Other invariant parameters could be used.

In any case, by interpreting a periodic vibration as a stiffness measure as in the "Myotonometer", local physical characteristics of surrounding should be also taken into account. Force measurements are already applied in gloves during physiotherapy. This is a valuable tool for quantification of physiotherapeutic treatment, but it provides no solution for measuring muscle stiffness/tissue hardness, since neither surrounding tissue nor displacement relative to initial tissue geometry is measured. A measurement system that assess muscle stiffness through mechanical parameters, inevitably interacts with that tissue, in the simplest case by additional systems required to position the probe onto the tissue.

Figure 4:
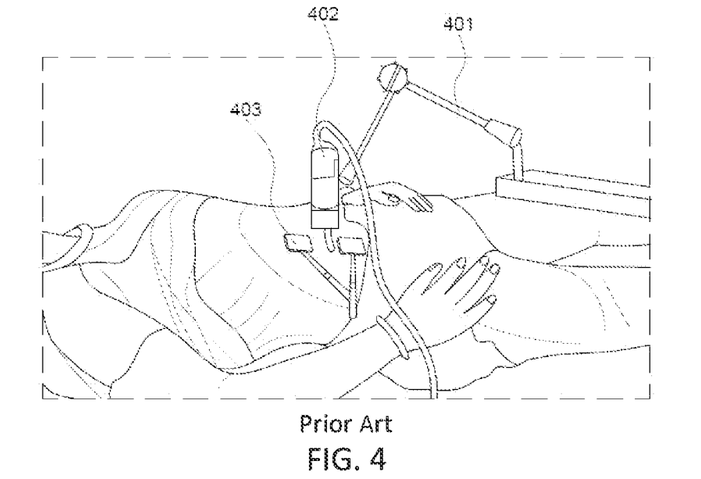
FIG. 4 illustrates a commercial tensiomyography device, as known from prior art.

Another solution comprises minimizing the effect of the probe on the tissue. For example, tensiomyography comprises measuring displacement in function of electrical stimulation. Tensiomyography is applied in a commercial setting to apply muscular functionality. FIG. 4 shows a prior art assembly comprising a control unit (not pictured), a tripod and manipulating hand forming a frame 401, a digital sensor 402, and electrodes 403.

In the abovementioned solution, interaction of measuring probe with the subject's body is virtually reduced to zero by placing body and probe in two separated fixed reference frames. The image of FIG. 4 was retrieved and adapted from http://www.tmg-bodyevolution.com/medical/functional-muscle-strain-diagnostics/, 29 Sep. 2017.

This reduction of interaction of the probe comes with the price that a complex measuring setting is required. Alternative solutions to decouple the effect of a probe onto the subject's body by built-in relative (device-to-skin) distance measurements include:

Structured light to assess relative displacement
Silicone carpet onto the subject's body surface that assess deformation in function of applied pressure Another option would be to minimize the interaction of the measurement probe with the subject's body. For example, the Vesmeter is one of the many devices to assess tissue at a point where the probe's interaction with the subject's body is minimal. This device is tailored to skin elasticity (Kuwahara Y, Shima Y, Shirayama D, Kawai M, Hagihara K, Hirano T, et al. "Quantification of hardness, elasticity and viscosity of the skin of patients with systemic sclerosis using a novel sensing device (Vesmeter): a proposal for a new outcome measurement procedure." Rheumatology. 2008; 47(7):1018-24). An outer ring detects skin contact, after which an inner probe measures relative displacement with respect to the outer ring and/or also corresponding counter force exerted by the tissue. However, the types of measurements enabled by this device are very limited, and there is a risk that the positioning system interferes with the act of sensing. In the Vesmeter, the force exerted on the outer ring is to be controlled by the operator. Furthermore, it has the disadvantage that position skew may occur, that only anisotropic measurements are obtained and that the measurements are limited to small forces on the inner probe, since bigger forces may induce a cave and thus contamination of the measurement.

SUMMARY OF THE INVENTION

It is an object of the present invention to provide standardized methods and systems for quantified measurement of tissue elasticity, e.g. muscle stiffness.

It is an advantage of embodiments of the present invention that tissue elasticity, e.g. muscle stiffness/tone, can be measured in a repeatable and calibrated way, where quantified data can be obtained accurately and with high resolution.

It is an advantage of embodiments of the present invention that tissue elasticity, e.g. muscle stiffness/tone, can be measured in a way that is easy and comfortable for both the operator and the subject.

It is an advantage of embodiments of the present invention that the time required for accurately measuring is limited. The system according to embodiments of the present invention is developed for, when applying it correctly, automatically obtaining a proper configuration for accurate measurements.

The present invention relates to a device for measuring elasticity of a tissue of an object, the device comprising
a base portion comprising contact means for contacting the device with the tissue,
a palpation probe for pushing down on the tissue the palpation probe comprising a palpation pen for pushing down the tissue and a force measuring means for determining a palpation force applied to the palpation probe and/or a displacement measuring means for determining a displacement of the palpation pen being representative for a displacement of the tissue, the palpation probe being positioned perpendicular to the base portion, and
a swivelling handle mounted pivotally to the base portion for positioning the device and for distributing a positioning force along the at least two contact points in a predetermined manner.

It is an advantage of embodiments of the present invention that standardized and accurate positioning of the device can be obtained, without additional effort. In this way, a user-friendly device is provided.

The swivelling handle may be pivotally connected to the center of the base portion or to equally distanced opposite sides of the center of the base portion. The swivelling handle may be pivotally connected to the system in the center of mass or the center of rotation of the system. The center of rotation may be a point where geometrically the rotation is most easy.

It is an advantage of embodiments of the present invention that, even if the device is not pushed down on with a perfect perpendicular force, only the perpendicular component of the force will be exerted on the subject's tissue measured, and the force is decomposed evenly on both contact points, thus resulting in a repeatable measurement.

The swivelling handle may be pivotally mounted with respect to the palpation probe.

The base portion may comprise a means for sensing contact with the tissue. The means for sensing contact may comprise at least one force sensor for sensing a positioning force applied to the base portion.

The medical device may comprise a compensation means for compensating the positioning force applied for positioning the device for the palpation force applied to the palpation probe.

It is an advantage of embodiments of the present invention that the force applied substantially perpendicularly to the subject with the aid of the swivel handle, can be kept constant at the contact points. Moreover, the force at both contact points is substantially equal, due to the swivel handle acting as a "reversed balance", resulting in a consistent measurement. Consistency and standardization entail enhanced measurement resolution.

The device furthermore, may comprise two sensors each positioned at one side of the palpation probe for verifying symmetry in the applied positioning force.

The device may comprise a feedback means for providing haptic and/or visual and/or auditory feedback for indicating the status of the measurement.

The contact means may further comprise contact surfaces, for example ring shaped or disc shaped surfaces.

It is an advantage of embodiments of the present invention that swivelling handle allows distributing a positioning force along both contact points in a predetermined manner.

The contact surfaces and the center of the palpation probe may be co-aligned.

The base portion may be adapted for being extendable such that the distance between the contact surfaces can be adapted so as to guarantee that the contact surfaces can be positioned outside an affected sink zone induced by the palpation.

It is an advantage of embodiments of the present invention that the device can be adapted to the size of the tissue to be measured, thus allowing to provide accurate measurements for different sized tissues, e.g. different types of muscles.

The palpation probe may comprise a spring for pressing down a palpation pen onto the object to be measured.

The force measuring means may comprise displacement measuring means such as a distance measurement sensor e.g. based on optical reflection detection, on a hall effect detection, on standing wave detection, on a sonar detection.

It is an advantage of embodiments of the present invention that existing distance measurement techniques can be applied for obtaining an accurate measurement of the displacement.

The device may be a device for muscle tone measurements.

The present invention also relates to the use of a device as described above, for any of evaluation of breast oedema, performing an EMG, performing muscle power quantification or performing dynamic measurements.

It is an advantage of embodiments of the present invention that reproducible measurements can be performed, allowing not only to obtain very accurate results, but also to evaluate a time evolution of tissue elasticity.

The present invention furthermore, relates to a method for calibrating a device as described above, the method comprising the steps of calibrating the sensor, calibrating the palpation pen by using calibration means comprising one or more reference pads for contacting the base portion and the palpation pen at a first and a second predetermined and different distance.

It is an advantage of embodiments of the present invention that the palpation pen and its displacement can be consistently calibrated, not only the sensor.

The method may further include calibrating the palpation pen by using a further reference pad for contacting the base portion and the palpation pen at a third distance between the first and a second predetermined and different distances, for example in the middle of the two.

It is an advantage of embodiments of the present invention that linearity can be ensured.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings. The drawings described are only schematic and are non-limiting. In the drawings, the size of some of the elements may be not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Figure 5:
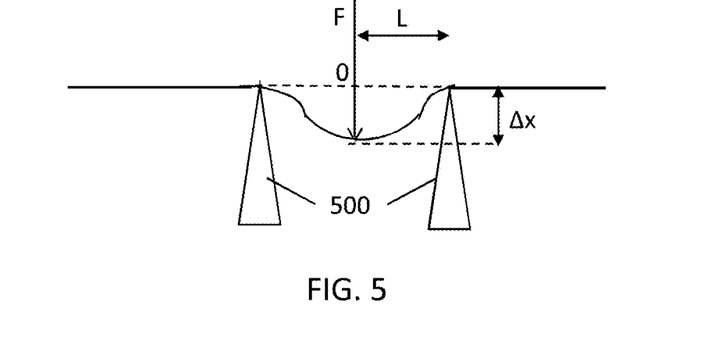
FIG. 5 illustrates the force and displacement of a string-like shaped body with clearly controlled end points.

In sport and health sciences and in the practice of physiotherapy, muscles are subject to local counter forces/deformations, inter alia due to underlying structures (bones) and overlying structures (skin, sub-cutis, etc.). Thus, judicious palpation is conducted, assessed and processed by the tacit knowledge of the physiotherapists in its judgement of muscle condition. For example, the endpoints of the muscle are relevant when interpreting a muscle as a string. Such model is shown in FIG. 5. The model mimics the local behaviour of the muscle by assuming there are support structures 500 at distance L of the point where the force is applied. If the string has uniform tension, the force constant k is proportional with the inverse of L. The uniform tension is then given by $$S = F \cdot L / \Delta x$$

This is only an approximation. For an accurate mapping, F, delta x and L should also be tracked, and the interaction between the measuring probe with the body should also be taken into account.

Embodiments of the present invention design the interaction of the measuring probe with the subject's body, even allowing quantifying it, in order to provide a model of how a physiotherapist might assess muscle stiffness. Embodiments of the present invention favour a mechanical solution with the potential to assess baselines, absolute levels as well as muscular changes, in contrast with existing techniques such as biofeedback, or measurement of electrical characteristics of actively applied current, which are limitative for tissue and muscular assessment. These techniques merely measure changes in muscular activity.

This solution is a valuable complementation to tensiomyography, to replace the external frame 401 shown in FIG. 4 used for recording displacement, and it might induce the development of compact hand-held devices for tensiomyography.

Embodiments of the present invention offer a solution to measure tissue elasticity and/or muscle stiffness/tone in a repeatable, calibrated way that is easy and comfortable for both operator and subject, and which can be included in a hand-held device.

Where in embodiments of the present invention reference is made to muscle tone, reference is made to hardness without the subject executing a deliberate, conscious contraction. In the present text, the terms muscle hardness, stiffness, or elasticity are used as synonyms.

However, the present invention is not limited to muscle tone measurement, and stiffness of other tissues can also be measured.

In a first aspect, the present invention relates to a device for measuring elasticity of a tissue of an object, for example a device for measuring elasticity of organic tissue. It comprises a base portion comprising contact means for contacting the tissue. It also comprises a palpation probe for pushing down on the tissue comprising a palpation pen for pushing down the tissue and a force measuring means for determining a palpation force applied to the palpation probe and/or a displacement measuring means for determining a displacement of the palpation pen being representative for a displacement of the tissue. The device also comprises a swivelling handle mounted pivotally to the base portion for positioning the device and for distributing a positioning force along the at least two contact points in a predetermined manner. Standard and optional features of a device according to embodiments of the present invention will now be described in more detail with reference to certain exemplary embodiments and with reference to the drawings, the invention not being limited thereto.

Figure 6:
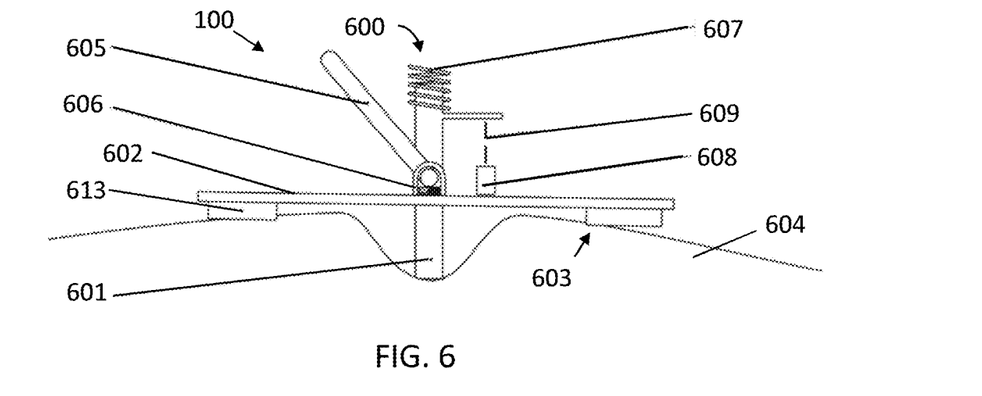
FIG. 6 illustrates technical scheme of an embodiment of the present invention.

FIG. 6 shows an outline of an exemplary embodiment of the present invention, showing a device 100 being used on a tissue 604, for example a muscle. The device 100 includes a palpation probe 600 for pushing down on the tissue. This palpation probe comprises a palpation pen 601 with a known area of contact, for contacting the surface of a tissue 604. Where in embodiments of the present invention reference is made to "palpation pen" or simply "pen", reference is made to a protrusion which serves as a pressure point for providing measurement (of e.g. stiffness) on a tissue. In some embodiments, the size and area of the pen may be adapted to the type of organism and to the type of tissue (long or flat muscles, cartilage, etc.). In one example, the pen has a diameter between 5 mm and 15 mm, e.g. 10 mm. The pen may have a domed tip, e.g. a dome of 2 mm high, for providing comfort and for allowing to follow the skin under pressure. The pen may have dimensions as known for conventional pen based systems. In some embodiments, the pen may be implemented at micron-scale, whereby accurate microsensors are implemented. Further, a force measuring means 608, such as a sensor, for sensing the force applied to the palpation pen on a tissue, or parameters related to that force, is included in the palpation probe 600, and may include counter-force elements, deformation sensors, pressure sensors, etc.

The device further includes a base portion 602 on which the probe 600 is mounted. The base may include means 603 for sensing contact with a tissue, specifically with the surface thereof, e.g. skin. For example, these means 603 may include one or more sensors that detect the moment at which contact takes place. These means 603 may assess the local interaction when a force is applied onto the tissue's surface and at the same time ensure a reproducible relative position of the device towards the subject's body. The device may include contact means 613, for example a shaped contact surface, or for example at least two contact surfaces or contact points, different from the palpation pen 601, for providing a reference contact between the device and the tissue.

The device further comprises a swivelling handle 605 mounted pivotally to the base portion 602. The handle 605 assists in positioning the medical device and distributing a predetermined force of the base portion 602 on the tissue 604 in a predetermined manner. This force is applied only in order to fix the position of the device, and it should be mild, e.g. not be so high that it disturbs the measurement. One example of a possible range of forces is 5N to 10N, although other forces also can be used. The range may be adjusted as function of the tissue. The swivelling handle 605 provides stability, repeatability and improvement of the accuracy of the palpation. Since the swiveling handle 605 is a separate handle not directly fixed to the palpation probe, the latter allows correct positioning of the system, without negatively influencing the palpation probe during the measurement. The latter allows to obtain an accurate measurement with an accurate direction of the palpation probe with respect to the surface at which a measurement needs to be performed.

For example, during use, the force applied on the tissue can be advantageously perpendicular (towards the plane formed by the surface of the tissue) and constant, including the contact or positioning force, so consistent and standardized measurements can be obtained. This entails enhanced measurement resolution.

In some embodiments, elastic means 607 is included in the probe 600 linked to the palpation pen 601. The elastic means 607 may provide a counterforce against the movement of the palpation pen 601 when the pen is applied on a tissue. The elastic means 607 may provide a consistent pressing force. The elastic means may be made swappable, in order to modify and personalize the interaction between the device and the tissue, if needed. It may be tuneable. For example, a torsion spring could be winded or unwinded to give more/less pressure. It may be a spring, such as coil spring, clip spring, compression or tension spring, torsion spring, etc. The elastic means 607 may be supported by the base portion 602.

In some embodiments, the elastic means 607 is an integral part of the force measuring means 608 (e.g. sensor). The force measuring means 608 may include means to measure the displacement of the palpation pen 601, so the force applied by the elastic means (whose elastic constant can be known) is in direct relation to the displacement of the palpation pen 601. This displacement is in turn measured by a displacement measuring means 609, e.g. an optical distance sensor that utilizes e.g. a beam of infrared light bouncing off a plate (e.g. reflective plate) situated along (e.g. at the center of) the pen. Other distance measurements might be considered as well: Hall sensors, standing waves, sonar based, etc. The output of the sensor for sensing the force of palpation can be corrected according to the output of the means 603 for sensing contact with the tissue, thus obtaining an accurate measurement of the muscle elasticity.

In some embodiments of the present invention, the base portion 602 may be a base plate. For example, it may be a wide plate. Its specific shape and geometry can be adapted according to the specific application or type of tissue to be tested. The base portion 602 has a structural function, and in some embodiments it may comprise a resilient material, presenting very low or no deformation under usual strains of the field of physiotherapy. The deformation may be minimal. The base portion may have reinforcement ribs on the inside and may be firmly screwed down in the device to prevent warping.

In some embodiments, the contact means 613 of the base may be for example two contact surfaces on two opposite sides of the base 601, in order to place them in two distant points of the surface of the tissue to be measured. For example, the contact points or surfaces may additionally serve to fix the position of the device. The contact points may include pads, ring-shaped surfaces, disc-shaped surfaces, plates with circular, oval shape, etc, with rugged surface, high friction surfaces, corrugated surfaces, dome-shaped, etc. Any suitable shape and composition which provide fixation to the tissue can be used. At least one of the contact means 613 may include sensors serving as means 603 for sensing contact. However, these means 603 do not need to be included in the contact means 613; for example the means 603 may comprise optical means for detecting whether contact between the base portion 602 takes place or not. The means 603 also may comprise other sensors to detect environmental conditions, such as for example temperature or moist.

The swiveling handle 605 acts as a reverse balance in the sense that the force is substantially equally distributed along two contact surfaces, regardless whether or not the swiveling handle 605 is pushed perpendicular onto the subject's body, for example the force distribution may be even. Thus, even if the device is not pushed down on with a perfect perpendicular force, only the perpendicular component of the force will be measured, thus resulting in an accurate measurement. Thus, with only two contact points, the interaction between the device 100 and the body is minimal, and still high accuracy can be obtained thanks to the handle 605.

The contact means 613 is not limited to two surfaces, and it may be an extended surface for example around the perimeter of the base portion 602, at a distance L of the palpation pen 601. In one embodiment two pads in a row on either side may be used. In another embodiment a ring or pressure pad underneath the entire surface could be used.

In some embodiments, where e.g. a two-contact point architecture is used, such an architecture strongly supports to have robust measurements, contact surfaces that can be moveable and measurements that can be sampled in time or as function of location. The latter assists in mapping or imaging of muscles.

In some embodiments of the present invention, the means 603 for sensing contact with the tissue may also measure the positioning or contact force. For example, a built-in force measurement for Fc can be included on the fixation zone, e.g. on the contact means 613. This improves stability and accuracy of the measurement, and it can be assessed that the inner probe and in particular its pen protrudes skin along the same direction. Thereby, the contact force on the fixation zone can be constant each measurement. This mild force registration Fc can be taken into account for the assessment of the force applied with the palpation probe. Ideally, the contact Fc force is equally distributed on the fixation zone, which can be provided by the two contact means 613 and the handle 605. Measuring Fc allows to monitor this distribution.

In some embodiments, the force needed to push in the palpation pen can be compensated with the measurement obtained with the force sensors included in the means 603 for sensing contact. This allows obtaining a tunable contact force, which is another important parameter describing stable and accurate palpation In some embodiments, the palpation probe 600 is positioned perpendicular to the base portion 602. In particular, the pen 601 of the probe 600 is positioned perpendicular to the base portion 602, ensuring a perpendicular application on the tissue.

In some embodiments, the dimensions of the pen (e.g. its length, or the area of its palpation surface) can be adapted, for example by swapping the pen, for targeting different applications.

FIG. 6 further shows that the means 603 for sensing contact with the surface of the tissue may be in line with the palpation probe 600, particularly the two contact surfaces acting as contact means 613 may be in line with the palpation pen 601. In that embodiment, the device is substantially placed on the subject's muscle 604, in the longitudinal direction of the muscle. In this particular case, the contact surfaces and the center of the palpation probe 600 (which includes the central pen 601) are co-aligned. This improves symmetry of measurement. However, the invention may not be limited thereto, and other configurations (e.g. using more than two contact points, some or all not being co-aligned) can be used.

Figure 13:
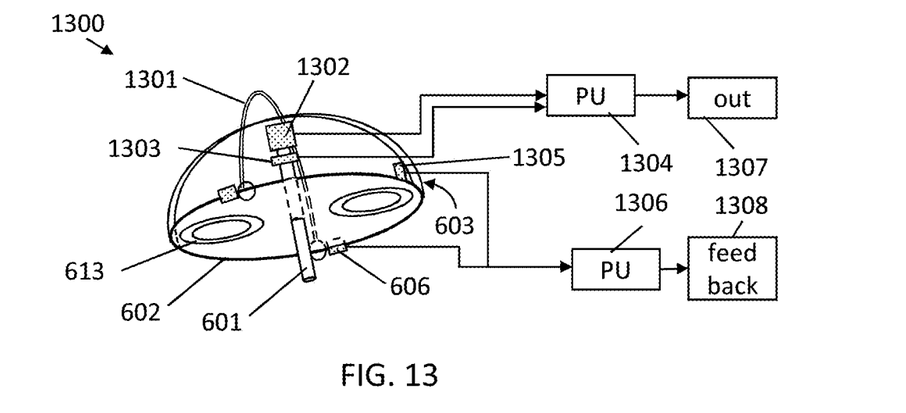
FIG. 13 illustrates a second prototype according to embodiments of the present invention.

In some embodiments of the present invention, the swivelling handle 605 can be pivotally connected to the centre of the base portion, or to opposite sides of the base portion; this is for example the case of the bow 1301 shown in FIG. 13. This layout has the advantage that only the perpendicular component of the force is measured, improving accuracy, even if the device is not pushed down on with a perfect perpendicular force.

In some embodiments of the present invention, the present invention not limited thereto, a small force sensor 606 can be placed in between the swiveling handle 605 and the base portion 602, e.g. below the brackets for which hold in place the handle 605 to the base portion 602. In some embodiments, the device may use two sensors 606 (one on each side, thus only one pictured in FIG. 6) to verify symmetry in the force applied with the pen 601. These sensors 606 may also measure parameters related to the positioning force applied via the handle.

In some embodiments, the symmetry of the positioning force can also be detected. For example, a sensor can be included in each of the two opposite sides of the palpation probe, and/or a sensor positioned at the contact means 613. For example, the force sensors 606 can be used to verify the symmetry of the positioning force, and/or the means 603 for sensing contact with the tissue surface can be used for sensing the symmetry. The output of these sensors advantageously provide reading of the symmetry of the positioning force.

The system may further include a feedback unit 1308, as shown in FIG. 13, for indicating the status of the measurement to the practitioner, and/or whether some corrections are required. It may for example indicate that the contact force is too high, or not high enough. It may provide also information regarding the symmetry of the force applied.

In order to perform a measurement, the device can be placed on the patient's skin, directly on top, at fixed position for palpation pin 601, for example, in the center of the muscle 604 to be measured.

The practitioner holds down the device, handling it by the swiveling handle 605, and pushes the pen 601 into the tissue.

If the device is not pushed down with a perfect perpendicular force, this will not affect the measurement at the palpation pen, since only the perpendicular component of the force is measured by the sensor. Further, only this force induces displacement of the muscle 604 and thus affects the measurement. Moreover, the swiveling will assure that the contact means 613 (e.g. two contact surfaces) are positioned onto the skin such that the base plate is substantially parallel to the subject's skin. Since the palpation pen 601 is attached substantially perpendicular onto the base plate 602, it also protrudes the muscle 604 perpendicularly.

In order to provide reliable measurement, the device should be properly fixed to the surface of the tissue. Fixation (zero distance between the device and the surface of the tissue) will be achieved by exerting (and/or registering) a mild contact force, or positioning force Fc, at the zone where the device is fixed against the tissue. In embodiments of the present invention, the tissue 604 can be fixed against the device 100 at a predetermined distance (L) around the palpation pen, such that the distance between the device (in particular the contact means 613 of the device) and the skin is zero at that distance.

Then, a palpation probe 600 or inner probe will measure displacement delta x as shown in FIG. 5 and counter force exerted by the muscle Fm. The present invention provides a standardized assessment of any impressible tissue or matter where palpation causes deformation. As already explained, if a muscle is modelled as a string, tension can be retrieved from force, displacement and L as F*L/delta x, independent on exerted contact force Fc at outer points of measuring probes (this is, at a sufficient length L from the central palpation probe); however, accuracy of the models of muscular condition improves by taking into account the parameters Fc, Fm, delta x and L. In some embodiments of the present invention, the parameters in the measurement can advantageously include the counter force induced by the tissue, the distance L from palpation pen 601 to contact surfaces, the force/pressure Fc at contact points at the moment of measurement, the dimensions of the palpation pen 601 and the force in function of displacement (delta x) of the palpation pen. By altering one or more of these parameters, different applications can be targeted, such as mechanical assessment of tissue at micron scale, soft matter assessment in material characterization, assessment of tissue (e.g. muscle) elasticity, etc.

The contact force Fc may be obtained by the means 603 for sensing contact with the tissue, while Fm and delta x can be obtained from the palpation probe 600. The distance L is a known value.

Figure 7:
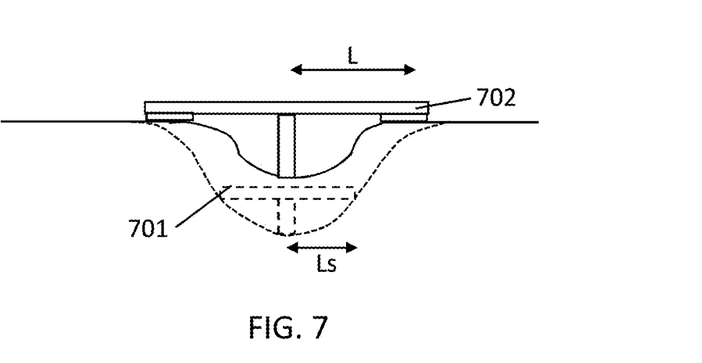
FIG. 7 illustrates a sink caused by a measurement probe, which could increase the apparent stiffness, and a preferred setup obtained by embodiments of the present invention.

In some embodiments of the present invention, the contact surfaces in the base portion are positioned far enough apart not to make contact with the affected sink zone in the center, as shown in the device with the base 702 in FIG. 7. In some embodiments, the distance L between the contact surfaces and the palpation pen 601 can be tuneable and registered according to the dimension of the muscle and type of measurement, to prevent measuring in a slumps caused by palpation, or control that effect. For example, the base may be extensible, or the contact surfaces may be adjustable, e.g. detachable and re-attachable, and repositionable so that the contact points can be positioned outside an affected sink zone induced by the palpation. FIG. 7 shows a comparison between two devices. the first device 701, in dashed lines, is too short (Ls), leading to a too high apparent stiffness. A better configuration of the base 702 is shown in solid lines, wherein the length L is increased, according to embodiments of the present invention. Thus, the device can be adapted to the size of the tissue to be measured, allowing accurate measurements for different sized tissues, e.g. different types of muscles, or even subjects.

Figure 8:
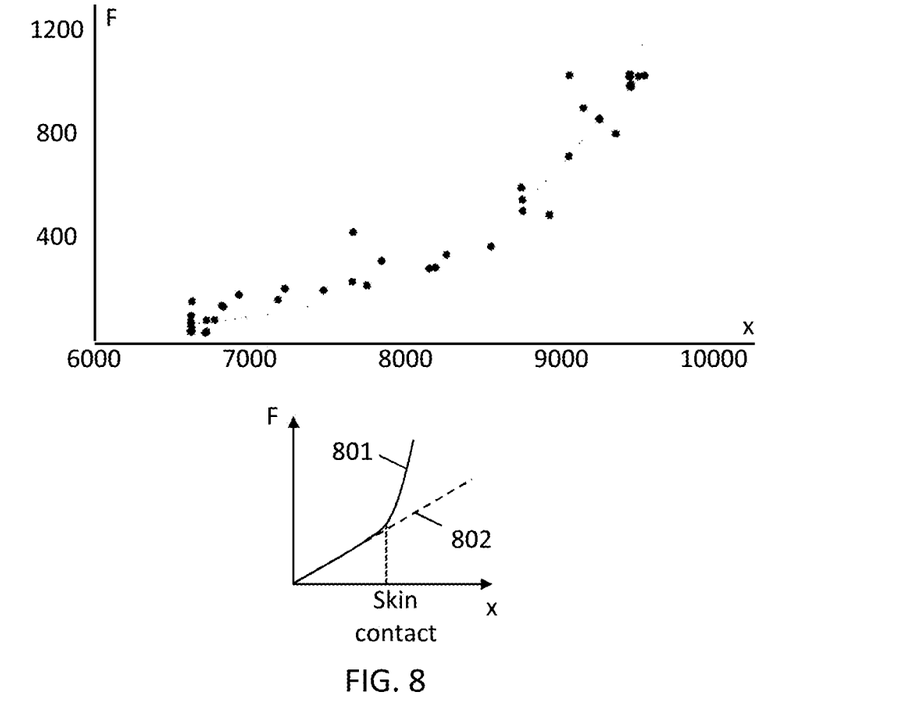
FIG. 8 illustrates the calibration curve and the deviation of the calibrated curve which quantify skin contact forces.

Additionally to the means 603 for sensing the contact with the tissue, some embodiments may include means to obtain the force-displacement curve and to obtain information regarding its deviation from a calibrated graph, as shown in FIG. 8. The upper drawing of FIG. 8 shows the calibration curve with displacement of palpation pen (abscissa) vs the measured force (ordinate). The lower drawing shows the deviation of the measured graph 801 with respect to the calibrated graph 802, in order to quantify skin contact forces (which may be contribute to the positioning forces. The values are retrieved from read out values on a micro controller for sensors (Arduino), and the graphs of FIG. 8 are given in arbitrary units.

Figure 9:
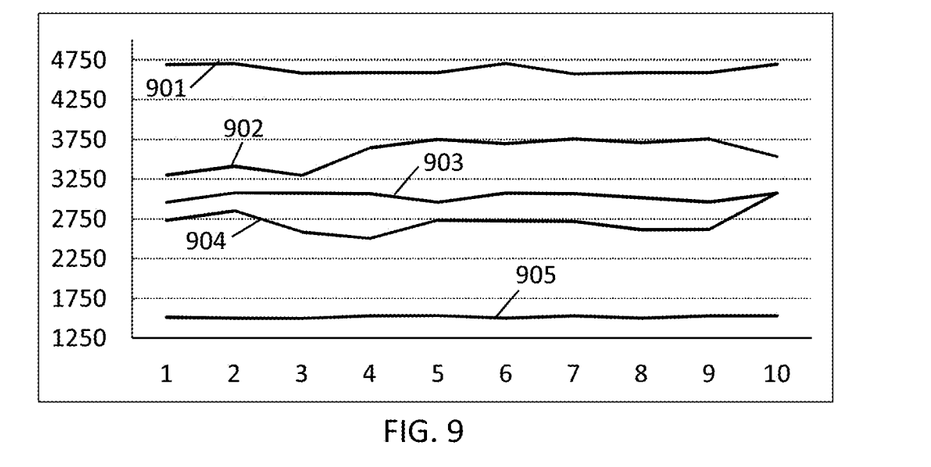
FIG. 9 illustrates different baseline data in 10 test sequences for surfaces with different stiffness.

FIG. 9 shows the baseline data in ten test sequences. The upper line 901 shows the results of tests performed on a hard surface, the second line 902 the results of tests performed on a tensed muscle, the third line 903 the results on a 3 cm foam, the fourth line 904 the results on a loose muscle and finally, the lowest line 905 shows the results on free air. The 5% inaccuracy in some of the results stems from tolerance on the position of the probe and force or distance measurements, but it is easily fixed by optimization of the positioning and measurements of distance and force. The optical displacement sensor may for example be replaced by force sensing, which is one to one related to the displacement. In any case, it is clear from the graph that the device is able to discriminate between measurements done on loose and tensioned muscle.

In summary, the device provides repeatable measurements, a good ground reference and stable contact surface, reducing or removing the influence of strain. Embodiments of the device can compensate and correct deviations in symmetry of positioning, and can correct even the positioning force. This can be provided in a small and portable device, very compact and user friendly. It is highly and easily customizable, both the device itself and the operation, to take account of personal parameters of the subjects, such as age, gender, socio economic situation, ethnicity, BMI, somatotype, etc.

In a further aspect of the present invention, the device is a device for performing muscle tone measurements. The device can be used as a medical or diagnostics device. The device can be used for performing EMG, for quantifying muscle power and performance, and dynamic measurements; however, applications of the device are not limited to sports and physiotherapy, and it can be applied to medical and health sciences. For example, it can be used to measure hardness or stiffness of tissues other than only muscular tissue, for example oedema (e.g. breast oedema), swelling, liquid retention in tissue, fat accumulation, etc.

All these uses and applications benefit from reproducible measurements with very accurate results, allowing additionally to evaluate the evolution of tissue elasticity, thanks to the reference provided by the device itself.

EXAMPLES

Figure 10:
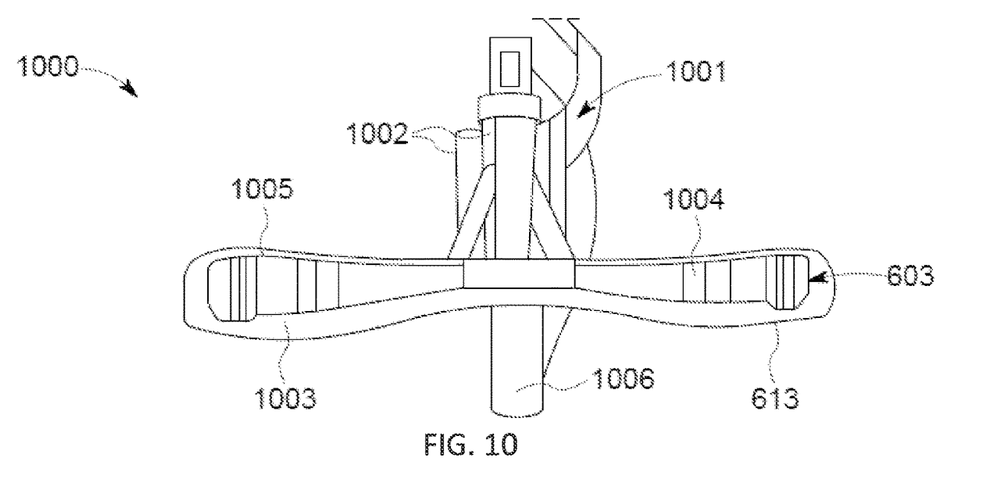
FIG. 10 illustrates a first prototype.

FIG. 10 shows an exemplary prototype 1000. The central probe 1001 is coupled to a series of springs 1002 with known (e.g. calibrated) force-displacement curve. Displacement is read out with a piezo electric sensor (not pictured), although other sensors may be used, such as optical sensors. A lower plate 1003 attached below is adapted to induce pressure at contact means 613 (e.g. fixation plates) as soon as skin contact occurs. For example, the lower plate may be slightly shaped as a clock-curve (e.g. very flat Gausian curve). Contact with the skin can be registered by means 603 for sensing contact with the tissue, for example by pressure sensors 1004 located between the lower plate 1003 and the upper part 1005, for sensing pressure, for example at the positioning or contact means 613 or at the lower plate 1003. The operator receives feedback on pressure, e.g. through an increase in lightening or via vibro tactile feedback, and the displacement of the pen 1006 of the central probe 1001 is measured only when a pre-set equal pressure is registered at both fixation points.

The first prototypes used a spring and force sensor to replicate the pressing of a practitioner's finger and the sense the practitioner will have in the form of resistance by the muscle. But since the pressure applied by the practitioner is in no way consistent/standardized, this method had no ground truth to which the measured tonus could be compared. For example, measurements depended on the angle in which the device was applied so the measured force was not consistent.

A further iteration was made using 3D printers and thus housed and fixated all sensor elements in a frame for standardized positioning onto the subject. It seems that this solved the issues of balance and ground truth, by adding a reference contact plane to the device. The reference contact plane consists of two contact areas spread apart by 100 mm. The palpating pen in the center was extended to probe out of the device. The probe comprised springs, but pulling springs (instead of pushing springs) were used to make the device smaller.

To maintain a consistent contact of the base plate with the skin, two pressure sensors can be attached on the contact areas (e.g. on the contact means 613) at either side of the device. Both sensors can measure forces from 200 to 2000 grams and have an accuracy of around 2.5 grams.

The probe extends through this base plate and thus will push into the subject's (e.g. patient's) skin and underlying muscles. In order to keep the device practical and pain free for the patient, the probe used can be swapped, thus providing a larger or smaller contact area of the specific muscle. The probe also can vary in length, which, in relation to the springs, determines the pressure applied to the palpating probe at a given consistent contact of the base plate.

An analog potentiometer is fixed to the base of the device and measures the height of the probe, so that information can be obtained on how deep the probe can be pushed into the patient's skin and muscle. Because the potentiometer is of an analog type, resolution is irrelevant (however, digital potentiometers can be used). In this case, the analog potentiometer has a range of 30 mm. The recording of the measurements by the potentiometer is performed by an analog-to-digital converter which has a resolution of 1024 points. This results in a theoretical physical resolution of 0.03 mm. In real conditions, friction and play (such as loosening of some of the elements) may limit actual resolution to about 0.07 mm. This combination of hardware parts where combined with a processing unit (e.g. an Arduino unit) and output means (e.g. a screen or display) to produce the first device ready for actual testing. This device ran on a custom code that calibrates the device every time it is powered up, waits for the researcher to confirm the start of a new measurement and then starts analyzing both force sensors in the base plate. These have to be within a fixed range of force (within 25 g of 450 g). As soon as this requirement is met, the device starts recording the measurements by the potentiometer on the palpation probe. These measurements are taken three times in a row with a delay of 25 ms in between measurements (in order to eliminate signal noise). These measurements again need to be within a fixed range (20, arbitrary unit) for the measurement to be valid.

Figure 11:
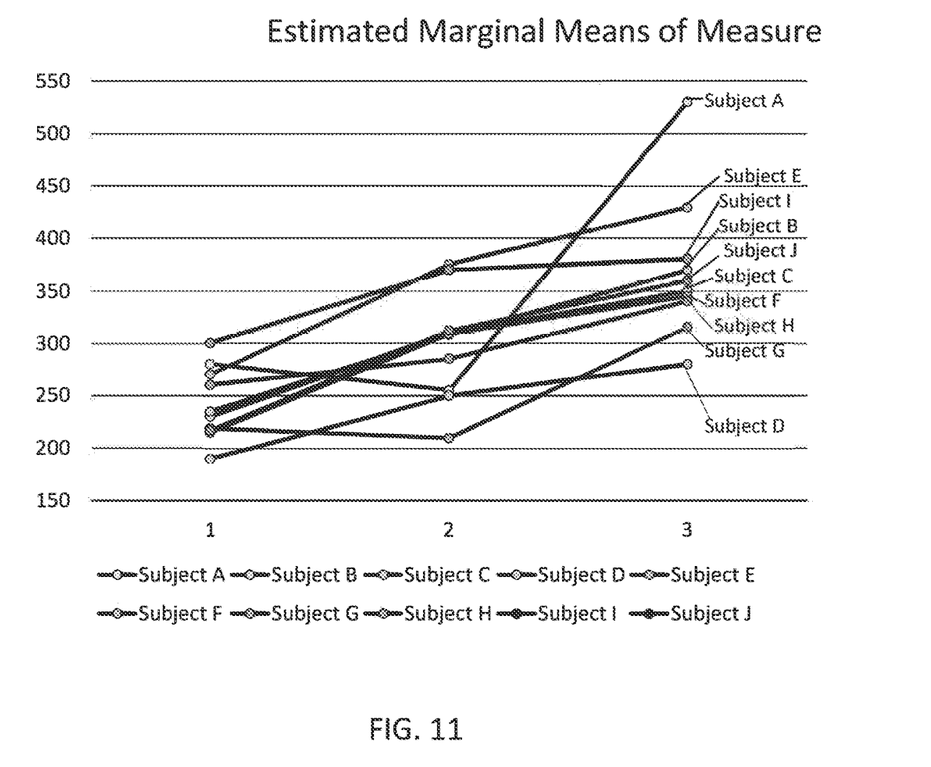
FIG. 11 illustrates the tension of a tissue (quadriceps) in 10 subjects for various conditions.

The first clinical trial study (pilot) has been conducted with 10 subjects by tensioning the subjected muscle (quadriceps femoris) in the extension of the knee. The tensioning was clearly measurable in the results shown in FIG. 11, showing the tension of the quadriceps in 10 subjects in rest (tension 1), 4 kg load (tension 2) and 1 repetition maximum (tension 3).

There is a high correlation between rest and 4 kg load (0.550) and between rest and 1 repetition maximum (1 RM) (0.695)

Further, the 10 healthy subjects performed were measured two times at rest and two times at 1 RM, with two weeks in between. There were no differences (paired t-test, $p>0.05$) and the intraclass correlation coefficients (ICC with Mixed model and consistency) were 0.864 ($p<0.001$) and 0.836 ($p=0.001$), respectively.

Figure 12:
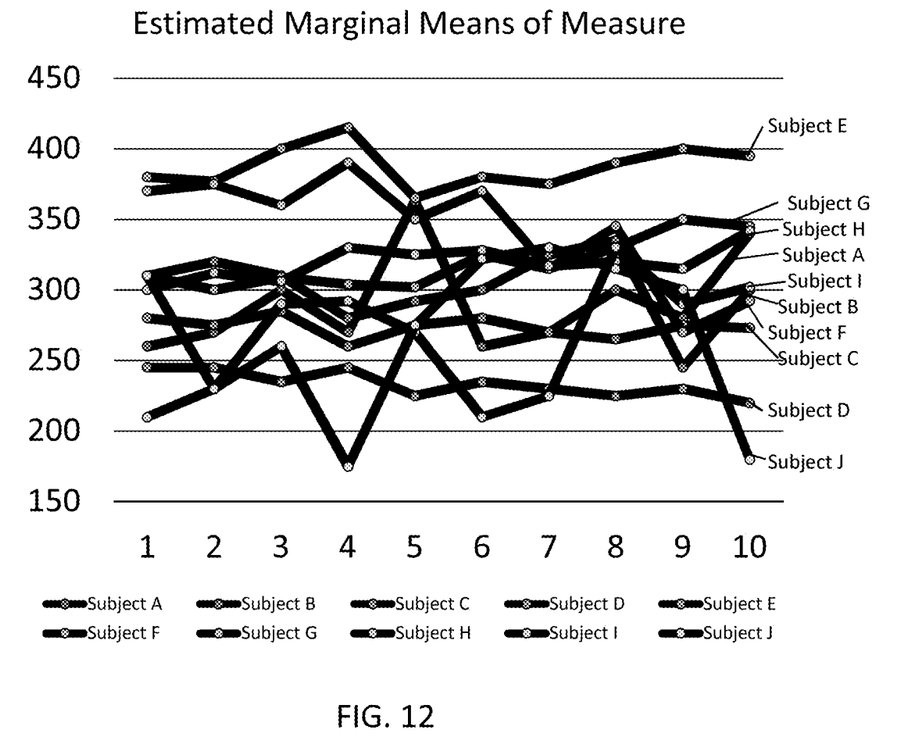
FIG. 12 illustrates the tension of a tissue (quadriceps) in 10 subjects under 10 repetitions.

For the load of 4 kg, the measures were repeated 10 times in two weeks, and the results are shown in the diagram of FIG. 12 for the tension of the quadriceps (10 subjects, 4 kg load, 10 repetitions). Also here no differences were found (SPSS, repeated measures anova: Greenhouse-Geisser p. 0.657), and the ICC was also very good (0.835 $p<0.001$).

Further analysis on the influence of the pressure applied to the base-plate and the measurement of the palpation probe revealed that the applied force has a significant effect on the palpation measurement.

The operator's responsibility to exert equal contact force on both fixation point hampers a quick measurement and usability/comfort for operator/subject. Moreover, perpendicular probing is only detected in the XY plane, allowing the device to be tilted along the "z direction" (perpendicular to the tissue).

In the exemplary device 1300 schematically shown in FIG. 13 according to embodiments of the present invention, two fixation or contact surfaces acting as contact means 613 (in this case plates) are placed substantially tangent onto the user's skin. To that end, the operator take hold of the device at a central bow 1301 (which acts analogously to the swiveling handle 605 of FIG. 6 and is pivotally connected to the center of the base 602) and presses it onto the subject's body while holding it between a pre-defined marked zone. A converse balance principle distributes the force applied by the operator along two steps. Firstly, the majority of the force is applied onto the pen 601 of the central probe. Secondly, as soon as one for the contact surface make contact with the subject's skin, the remaining force is immediately distributed over both contact surfaces, which are both thus placed tangent onto the subject's body and with equal force.

More specifically, a sensor 1302 senses the force applied on the palpation probe. The same sensor or a different sensing means 1303 may additionally sense the displacement of the palpation pen 601. The signals can be sent to a processing unit 1304. In order to provide means 603 for sensing contact with the tissue, one or two sensors 1305 may sense the positioning force applied, ensuring that the positioning is effective and repeatable (for example, not allowing the system to record a measurement unless the positioning force is within a predetermined range). For example, the positioning sensors 1305 may comprise sensing means at the contact means 613. For example, they may be pressure or force sensors, which may measure forces from 200 to 2000 grams and have an accuracy of around 2.5 grams, as explained above. The recorded positioning force can also be used to compensate the measurement of the palpation force, by correction of the measured force.

Tilting along z-direction is controlled by splitting the force along left and right side, assessing it on both sides and comparing both split forces. They are equal if and only if the device has zero z-tilt. This perpendicularity is controlled by reverse balance principle and equality of split forces, provided by the central bow 1301 pivotally connected to the base 602. In case two contact surfaces are used as contact means 613, the sensors may also be used to ensure that the positioning force is symmetrical, e.g. applied equally in two contact surfaces. Optional sensors may be included, like the small sensors 606 between the central bow 1301 and the base 602, further improving symmetry and compensation. In some embodiments, feedback on z-tilt can be provided, for example including force sensors 606 and haptic (e.g. vibrotactile) and/or visual and/or auditory feedback. For example, the signals of the force sensors 606 are sent to a processing unit 1306, which may be the same as the unit of the sensor or sensors 1302, 1303 of the palpitation probe, or may be different. An output means 1307 connected to the processing unit 1304, such as a display, can give the results of the palpation force, for example after compensation from the positioning force. Another output 1308 may give optical signals or haptic feedback to ensure symmetry of the positioning. Additionally, the results of the positioning force may also be visualized with a display.

Other compensation and/or feedback means providing compensation for the positioning force can be included in the base 602 of the device itself, for example sensors with visual signals that indicate that both contact surfaces are being pressed with the same force against the subject. Other feedback means may be tactile vibrofeedback.

Calibration.

Differences in production tolerances, machining operations and variations in electric component may introduce variation in the measurements. Thus, calibration can be applied during or after device assembly.

Figure 14:
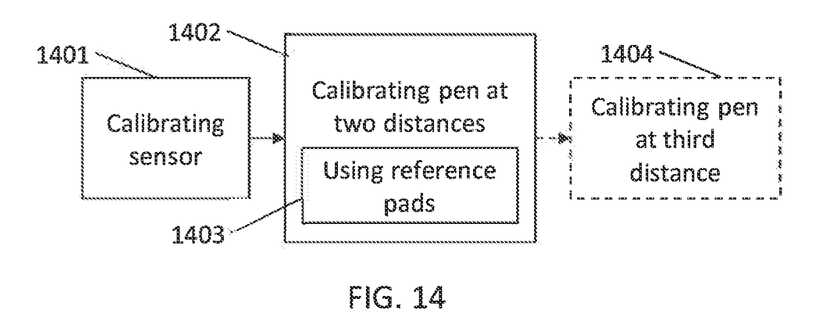
FIG. 14 illustrates an exemplary method of calibration of a device according to embodiments of the present invention.

In order to calibrate and verify the optimal measurement of the palpation devices, a standardized method can be defined. An exemplary method is shown in the flowchart of FIG. 14. The method comprises calibrating 1401 the sensor 608, calibrating 1402 the pen 601 by using 1403 one or more reference pads for contacting the base portion 602 (e.g. the contact means 613) and for contacting, at one or more different predetermined distances from the base portion 602, the pen 601. These pads 1501, 1502, 1503 are shown in the upper picture 1500 of FIG. 15. The method can optionally include calibrating 1404 the pen 601 at a third distance, in between the other two, for example at half the one or more different predetermined distances.

More in detail, first the measuring force is defined. This means the force at which two reference surfaces would signal that the correct force has been applied. In order to reach a consistent force all sensors are on by one applied a fixed load to of 150 gr. The readout of the sensor is captured and fixed in the code of that device as the reference force. Sensors can be separately calibrated 1401 for this.

TABLE I

Results for the sensor calibration of three devices

| | Blue A | Blue B | Green A | Green B | Grey A | Grey B |
|---|---|---|---|---|---|---|
| Measurement | 400 | 900 | 1200 | 800 | 550 | 530 |

Differences in these sensors are a normal, since they always need to be calibrated at first use.

Then, the palpation pen can further be calibrated 1402. In order to calibrate these, a set reference pads 1501, 1502 are used. For optimal consistency, using foam pads or soft materials is not optimal, since they always have variance. Thus, the reference pads are preferably resilient and/or undeformable.

Figure 15:
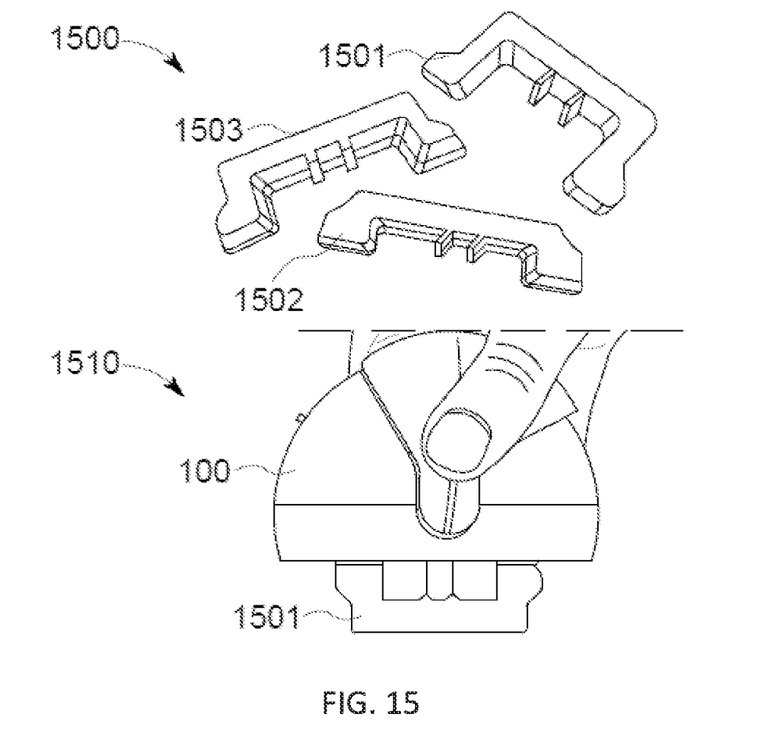
FIG. 15 illustrates calibration pads suitable for the calibration method, and a calibration step.

The device 100 is placed, as shown in the lower picture 1510 of FIG. 15, on the reference pad 1501 that provides highest distance (maximum extension of the pen 601) and its recording is noted, then placed in the pad 1502 providing the lowest distance and again noted. The distances are indicative of the amount of displacement the pen 601 would endure, and they are related to a value of stiffness on a tissue. These two values will be used to linearly map the sensor to a fixed reference calibration value.

TABLE II

Results of the calibration using high pads and low pads.

| | Blue A | Green A | Grey A | Calibration to |
|---|---|---|---|---|
| High measurement | 90 | 75 | 78 | 80 |
| Low measurement | 3089 | 3260 | 3180 | 3200 |

Assuming that the measurement in between would remain linear, this calibration is sufficient. The results can be compensated in the analysis software, for example.

Optionally, in order to be certain about the linearity a third reference pad 1503 is used to validate the halfway point of the stroke.

TABLE III

Results of the calibration for linearity using a third pad.

| | Blue A | Green A | Grey A | Expected |
|---|---|---|---|---|
| Halfway point | 1823 | 1816 | 1819 | 1820 |

The invention claimed is:

1. A kit including a device for measuring elasticity of a tissue of an object and a calibration means for calibrating a palpation pen of the device, the device comprising:
    a base portion comprising contact means for contacting the device in at least two contact points with the tissue,
    a palpation probe comprising the palpation pen for pushing down the tissue and comprising a force measuring means for determining a palpation force applied to the palpation probe and/or a displacement measuring means for determining a displacement of the palpation pen being representative for a displacement of the tissue, the palpation probe being positioned perpendicular to the base portion, and
    a swivelling handle mounted pivotally to the base portion for positioning the device and for distributing a positioning force along the at least two contact points in a predetermined manner, and
    the calibration means for calibrating the palpation pen, the calibration means comprising one or more reference pads positioned for contacting the base portion and the palpation pen at a first and a second predetermined distance.

2. The kit according to claim 1, where the swivelling handle is pivotally connected to a center of the base portion or to equally distanced opposite sides of the center of the base portion.

3. The kit according to claim 1, wherein the swivelling handle is pivotally mounted with respect to the palpation probe.

4. The kit according to claim 1, wherein the base portion comprises means for sensing contact with the tissue.

5. The kit according to claim 4, wherein the means for sensing contact comprises at least one force sensor for sensing a positioning force applied to the base portion.

6. The kit according to claim 1, wherein the device comprises a feedback means for providing haptic and/or visual and/or auditory feedback for indicating a status of the measurement of the elasticity of the tissue of the object.

7. The kit according to claim 1, wherein the contact means further comprise contact surfaces.

8. The kit according to claim 7, wherein the contact surfaces and a center of the palpation probe are co-aligned.

9. The kit according to claim 7, wherein the base portion is adapted for being extendable such that a distance between the contact surfaces can be adapted so as to guarantee that the contact surfaces can be positioned outside an affected sink zone induced by the pushing down of the tissue.

10. The kit according to claim 1, wherein the palpation probe comprises a spring for pressing down the palpation pen onto the object to be measured.

11. The kit according to claim 1, wherein the displacement measuring means comprises a distance measurement sensor based on optical reflection detection, on a hall effect detection, on standing wave detection, or on a sonar detection.

12. The kit according to claim 1, wherein the device is a device for muscle tone measurements.

13. A use of the kit according to claim 1, for assisting in any of evaluation of breast oedema, performing an EMG, performing muscle power quantification or performing dynamic measurements, the use comprising:

contacting the device with the tissue, pushing down the tissue with the palpation pen of the palpation probe,         determining the palpation force applied to the palpation probe and/or determining the displacement of the palpation pen being representative for the displacement of the tissue, the palpation probe being positioned perpendicular to the base portion, and     positioning the device and distributing a positioning force along the at least two contact points in the predetermined manner with the swivelling handle mounted pivotally to the base portion.

14. A method for calibrating a device for measuring elasticity of a tissue of an object, the device comprising:

a base portion comprising contact means for contacting the device in at least two contact points with the tissue,     a palpation probe comprising a palpation pen for pushing down the tissue and comprising a force measuring means for determining a palpation force applied to the palpation probe and/or the displacement measuring means for determining a displacement of the palpation pen being representative for a displacement of the tissue, the palpation probe being positioned perpendicular to the base portion, and     a swivelling handle mounted pivotally to the base portion for positioning the device and for distributing a positioning force along the at least two contact points in a predetermined manner, the method comprising the steps of calibrating the force measuring means and/or displacement measuring means, calibrating the palpation pen by using calibration means comprising one or more reference pads positioned for contacting the base portion and the palpation pen at a first predetermined distance and a second predetermined and different distance.

15. The method of claim 14, further including calibrating the palpation pen by using a further reference pad for contacting the base portion and the palpation pen at a third distance between the first predetermined distance and the second predetermined and different distance in a middle of the first predetermined distance and the second predetermined distance.

* * * * *